United States Patent [19]
Murbach et al.

[11] Patent Number: 4,549,428
[45] Date of Patent: Oct. 29, 1985

[54] DEVICE FOR THE DETERMINATION OF THE AMOUNT OF SUBSTANCE OR THE DENSITY OF FIBER STRUCTURES

[75] Inventors: Erwin Murbach, Naenikon; Jean Peter, Moenchaltorf, both of Switzerland

[73] Assignee: Zellweger Uster Ltd., Uster, Switzerland

[21] Appl. No.: 468,188

[22] Filed: Feb. 22, 1983

[30] Foreign Application Priority Data

Feb. 19, 1982 [CH] Switzerland .................. 1040/82

[51] Int. Cl.$^4$ .................. D01H 5/38; G01N 9/26
[52] U.S. Cl. .................. 73/32 R; 73/37.7; 73/160; 19/240
[58] Field of Search .................. 73/32 R, 37.7, 160; 19/240

[56] References Cited

U.S. PATENT DOCUMENTS

| | | | |
|---|---|---|---|
| 3,752,170 | 8/1973 | Murbach | 73/37.7 |
| 3,822,590 | 7/1974 | Tharpe et al. | 19/240 |
| 3,938,223 | 2/1976 | Grice | 73/32 R |
| 4,121,450 | 10/1978 | Zurcher | 73/32 R |
| 4,184,361 | 1/1980 | Erben | 73/37.7 |

Primary Examiner—Stewart J. Levy
Assistant Examiner—John E. Chapman, Jr.
Attorney, Agent, or Firm—Antonelli, Terry & Wands

[57] ABSTRACT

Device for the determination of the amount of substance or the density of fiber structures, which utilizes the elastic properties of the fiber material. By means of a sphere which is positioned in a conical opening in a duct through which the fibers pass and which presses on the fibers with a part of its surface, a nozzle is throttled, so that the pressure on the nozzle represents a measure for the force on the sphere. This pressure is in a definite relationship to the fiber pressure on the sphere and can be measured with a pressure measuring device and transformed into an electrical signal by means of a normal commercially-available converter. A small groove in the wall of the duct behind the sphere avoids the attachment of fibers between the sphere and the opening.

10 Claims, 8 Drawing Figures

DEVICE FOR THE DETERMINATION OF THE AMOUNT OF SUBSTANCE OR THE DENSITY OF FIBER STRUCTURES

FIELD OF THE INVENTION

The present invention relates in general to devices of the textile industry, and more particularly, to a device for the determination of the amount of substance or the density of fiber structures, especially of the substance cross section of slivers.

BACKGROUND OF THE INVENTION

In the textile industry, the determination of the amount of the substance of fiber structures, in particular the cross-sectional substance, is very important. The cross-sectional substance of slivers is of considerable importance in the processing thereof to form yarn, because this cross-sectional substance directly influences the fineness of the yarn and the evenness of the cross-sectional regularity thereof.

Primarily, a measurement of the substance or density of a fiber quantity involves a determination of the amount of substance of a fiber structure, without taking into account whether the fiber is moving or stationary. In this regard, the measurement of moving slivers does not differ in principle from the measurement of stationary slivers, only the parts which guide and limit the slivers must be correspondingly adapted.

The determination of substance in a direct manner, such as by weighing, is practically impossible, particularly on running slivers. For this reason, different proposals for the solution of this problem have been advanced which are based on the indirect measurement of cross-sectional substance. Such proposals have involved purely mechanical measurement by means of a grooved roller and a feeler roller, the use of optical measuring devices which utilize the absorption or reflection capacity of the slivers, and acoustic measuring devices. All of these approaches have proven to be undesirable or unsatisfactory for one reason or another.

The so-called active-pneumatic measuring device must also be mentioned as another method of determining the substance cross section of slivers. This measuring device essentially comprises a funnel, to the side of which is connected a pressure measuring device. When a sliver passes through the funnel, pressure variations are caused on this lateral connection, which are transformed into equivalent signals which correspond to the cross section of the sliver. This active-pneumatic measuring device is, in itself, of simple design and very easy to install; however, it has the disadvantage that the measured values are dependent both on the fineness of the fiber (micron-air value) and on the speed of movement of the sliver.

Extensive work has also taken place to determine the elasticity of a sliver passing through a duct having defined dimensions. With this method, the sliver is regarded as a spring, which builds up a system of mechanical oscillations, together with the mass of the sliver. Thus, the resonance frequency of the system on the one hand or the transit time of oscillation pulses on the other hand produce a measure of the substance amount or density of the fibers. A process of this type and the appropriate devices for the determination of the amount of substance or the density of quantities of fibers based on the utilization of the elastic properties of the material have been described, for example, in U.S. Application Ser. No. 384,942, filed June 4, 1982. The disadvantage of this process and the related devices is the high cost of the generator, receiver and the auxiliary equipment for the determination of the amount of substance of the fiber material.

BRIEF DESCRIPTION OF THE INVENTION

The present invention is also based on a determination of the elasticity of a sliver passing through a duct, and therefore, relies on similar concepts utilized in the method and apparatus disclosed in the afore-mentioned U.S. Application Ser. No. 384,942. However, in accordance with the present invention, the measurement of the amount of substance of fiber material is effected without the need for the complicated and expensive generator, receiver and auxiliary equipment required by the prior method.

In particular, the present invention provides a measuring device which includes a duct through which the quantity of fibers passes, the duct having an opening in the side thereof in which a passive body, such as a sphere, is supported so that part of the passive body extends into the duct and into contact with the fibers therein. The passive body is therefore subjected to a force directed outwardly of the duct, which force is proportional to the elasticity of the fiber quantity. A force is then applied to the passive body to place it in a state of equilibrium, and this last-mentioned force is measured to provide a measure of the substance quantity of fibers.

The equilibrium producing force may be provided in various ways; however, special advantages result from the use of compressed air applied to the passive body through a nozzle positioned in spaced relationship thereto. In this regard, the compressed air not only provides the required equilibrium producing force, but also helps to keep the apparatus clean of particles and dust.

These and other features and advantages of the present invention will become more apparent from the following more detailed description of various embodiments illustrated in the accompanying drawings.

DETAILED DESCRIPTION OF THE PREFERRED EMBODIMENTS

Figure 1:
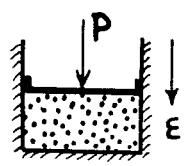
FIG. 1 is a schematic diagram of the basic principle of the measuring process.
Figure 2:
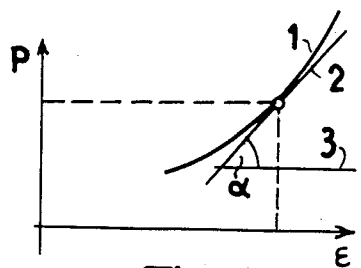
FIG. 2 is a force-elongation diagram.

Textile fiber structures are, as a rule, a structure of fibers with a very large intermediate air space. Under moderate pressure, the amount of material only (amount of substance) of the fibers in relation to the cross-sectional size thereof is relatively small. In the funnels of carding machines, for instance, this amounts only to 10–20%. When a loosely formed quantity of fibers is pressed (FIG. 1), a certain force-elongation characteristic (FIG. 2) results. As no tension can be applied to the quantity of fibers by this means but only compression, the resulting elongation $\epsilon$ corresponds to the applied compression. This differs from the generally-accepted force-elongation diagrams of solid bodies. According to the graphic representation in FIG. 2, the elongation $\epsilon$ (compression) is shown in the direction of the abscissa and the force P in the direction of the ordinate as curve 1.

The modulus of elasticity E may be expressed in the usual way at each point by the tangent of the angle $\alpha$, which is embraced by the tangent line 2, applied to the curve at the point in question, and the horizontal 3:

$E = \tan \alpha$

Observations have shown that a specific force, and thus a specific modulus of elasticity E, corresponds to a specific density of the fiber quantity. In this context, the term "density of the fiber quantity" is understood to mean the average taken from the mixture of fibrous material and the air in the interspaces of the fibrous material. Thus, it holds true that the pure substance cross section $Q_o$ of the sliver equals the cross section Q of the sliver times the space factor F.

Changes in the force, or in the modulus of elasticity, as a function of the density are very distinct. From this, it is apparent that when, at any point, the total quantity of fibers occupies a defined space or cross section, then the compressive force can be determined, and from that, the density can be calculated. From the density and the defined space or cross section, the pure material quantity can be determined.

It must, however, be emphasized that the force or the modulus of elasticity, as a function of the compression, usually produces different results for several measurements taken on the same quantity of fibers, as a rule. Above all, the first compression of a loose quantity of fibers requires more force than is necessary for subsequent compressions. For the purpose of the determination of the amount of substance in fiber structures, it is advantageous to evaluate only the results of the first compression or only the results of repeated compressions. During this procedure, it is particularly advantageous to determine the compression in pipes or in the area of funnels of carding or drawing or similar machines, because, at these points, the fiber structures are in the process of being continuously converted from a loose state into a more concentrated state, and thus, the first compression is occuring at that point. A further advantage of such point of measurement lies in the fact that the outer cross section of the sliver can be exactly defined. Since this application certainly constitutes the most frequent use of the measuring device, according to the invention, in the ensuing disclosure, measuring arrangements will be explained for determining the amount of substance of slivers which pass through a duct of defined cross section. In principle, these considerations also apply to measurements on stationary material in an exactly defined space.

Figure 3:
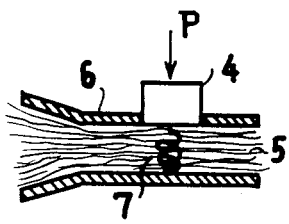
FIG. 3 is a diagram of a measuring system with a cubic measuring body.
Figure 4:
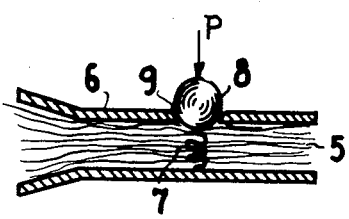
FIG. 4 is a diagram of the same system as FIG. 3 with a spherical measuring body.

The function of the measuring device according to the invention can be explained with the aid of FIGS. 3 and 4 as follows. The measuring body 4, which is fitted in the side of the duct 6 containing the fiber material 5, presses on the fiber material 5, which due to its elastic properties, can be described as a spring 7 acting against the measuring body. In FIG. 4, it can be seen that the measuring body projecting into the fiber material 5 consists of a sphere 8, which comes into contact with the fiber material through an opening 9 in the wall of the duct 6. This narrows the cross section of the duct 6. Through this, the elasticity of the fiber material 5 comes into effect, by which the sphere 8 is pressed outwards. This yielding of the sphere, according to the invention, is opposed by a counter force P on the sphere 8, so that a defined point of equilibrium of the sphere 8 is obtained, which is dependent on the elasticity of the fiber material 5. The force P set up is then a measure of the amount of fibers in the cross section of the duct.

Preferably, the force P on the sphere 8 is produced pneumatically. However, any other sort of effective force can be applied to the sphere 8, such as, for example, electrical or magnetic forces. In every case, it must be possible to determine, as a characteristic parameter of the amount of fiber, either the force resulting from a defined point of equilibrium or the point of equilibrium of the sphere 8 resulting from a defined force in a direction transverse to the axis of the duct.

Figure 5:
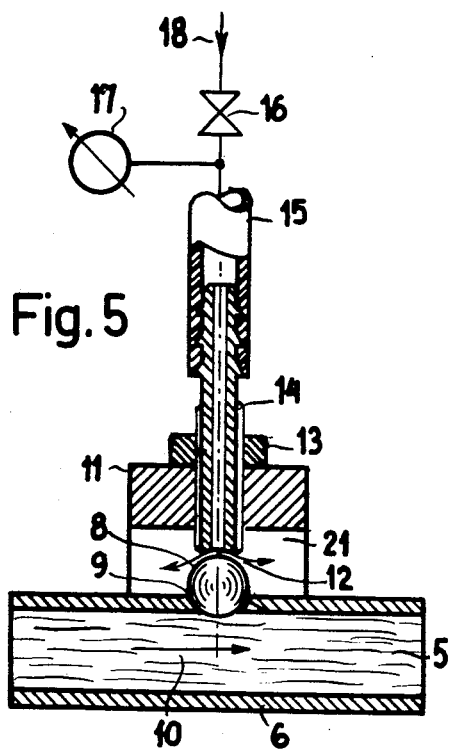
FIG. 5 is a longitudinal sectional view of a practical version of the measuring device.
Figure 6:
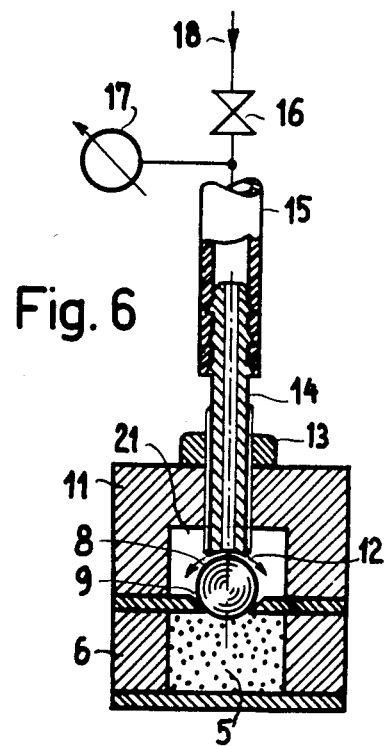
FIG. 6 is an end sectional view of the same measuring device illustrated in FIG. 5.

FIGS. 5 and 6 show in longitudinal and transverse cross section, respectively, an example of a version of such a measuring device operated pneumatically. The duct 6 can be seen through which the fiber material 5 passes in the direction of the arrow 10. The sphere 8 reposes in the annular, spherical opening 9.

A nozzle tube 14 is screwed into a yoke 11, which is suitably mounted on the duct 6, and the tube 14 is fastened in position by means of a lock nut 13. In this regard, the tube 14 is adjusted in position so that there is sufficient play between the sphere 8 and the outlet of the nozzle 12, to permit the formation of an annular air gap therebetween through which the compressed air introduced through the nozzle 12 can escape. The intake of this compressed air is from a source of compressed air 18. A stream of air is fed through throttle 16, a pipe 15 and the nozzle tube 14 to the nozzle 12.

Through the resilience of the sliver, the sphere 8 is pressed against the nozzle 12, and the size of the air gap between the nozzle 12 and the sphere 8 adjusts itself automatically so that the pressure in the pipe between the sphere and the throttle exactly compensates for the compression of the sliver. This pressure is a measure for the fiber cross section. It can be measured by means of the pressure measuring device 17 and transformed into proportionate electrical signals by means of a normal converter. The air gap itself is, therefore, determined by the amount of the pressure of the fiber material on the sphere 8, so that the pressure on the measuring device 17 is in an exactly-defined relationship to the amount of fiber 5 which is in the duct 6 at the time. The maximum size of the air gap is determined by the initial setting of the depth to which the nozzle tube 14 is screwed into the yoke 11.

The advantage of the arrangement according to FIGS. 5 and 6 lies in the fact that the spherical body serves simultaneously in the simplest way as the receiver for the force and as a pressure regulator, and that the air, which is the measuring medium, simultaneously acts as an air support and also as a cleaning medium for the measuring body.

It can also be regarded as an advantage that the air introduced through the nozzle 12 does not get past the sphere 8 into the fiber material 5 and if this does occur, only a small part of the air enters into the fibers. The largest part escapes outside the parts guiding the fibers in the space 21 and thus removes any deposits which may be left.

Figure 7:
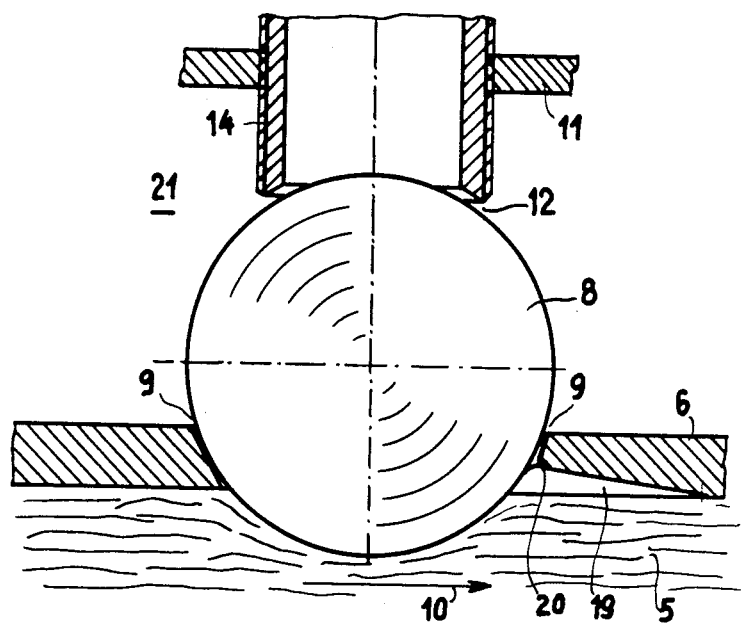
FIG. 7 is a partial view in longitudinal section of an enlarged section of FIG. 6.
Figure 8:
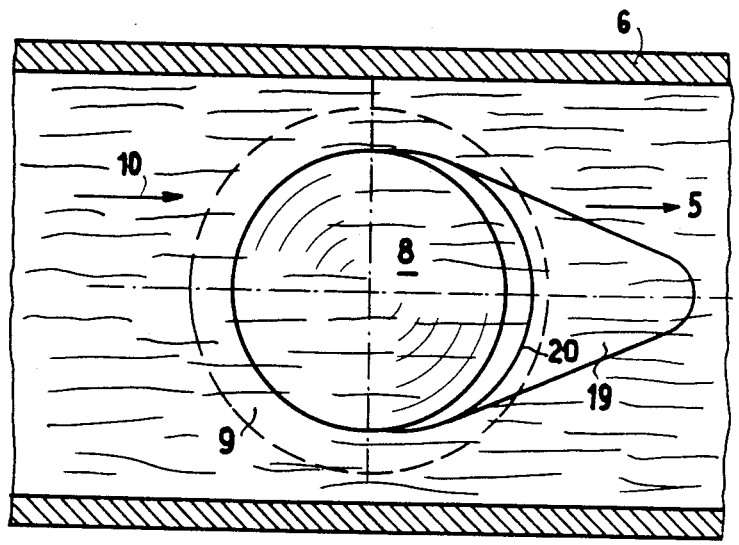
FIG. 8 is a bottom view of the device of FIG. 6.

In order to avoid the retention of fiber material in the annular gap between the wall of the duct and the sphere 8, which could lead to errors in results, one of the measures shown in FIGS. 7 and 8 can be utilized. In the conical, annular opening 9 in which the sphere 8 is supported, a groove 19 is milled, with a polished edge 20, in the direction of flow of the fiber material, the axis of the groove being inclined towards the axis of the duct, so as to have maximum depth at the edge of the opening 9. Through this, fibers which have penetrated into the annular gap, are drawn to the rear side of the sphere 8 during their passage and are released there, as the annular gap is interrupted by the groove 19.

It is important that, for trouble-free operation of the device according to the invention, the sphere 8 is accommodated on the side situated outside the duct 6 by an adequately-large space which leads to the free atmosphere, so that any particles of fiber or dust can be carried away by the air flowing through the nozzle 12. In this way, faultless operation of the measuring system is assured, without the need for constant maintenance.

While we have shown and described several embodiments in accordance with the present invention, it is undersood that the same is not limited thereto but is susceptible of numerous changes and modifications as known to a person skilled in the art, and I therefore do not wish to be limited to the details shown and described herein but intend to cover all such changes and modifications as are obvious to one of ordinary skill in the art.

What is claimed is:

1. An apparatus for determining the substance amount or density of quantities of fibers, comprising
    guide means including a duct for guiding said quantity of fibers through a space of predetermined constant cross section in said duct, said duct having an opening in the side thereof in communication with said space;
    a passive body disposed in said opening in said duct so as to partly extend into said duct and thereby be subjected to an outwardly-directed pressure from said fibers in the radial direction of said duct, which pressure is proportional to the elasticity of the fibers in said duct for a group of fibers having said predetermined cross section;
    means for subjecting said passive body to a variable inwardly-directed pressure in the radial direction of said duct to place said passive body in a state of equilibrium with respect to said outwardly-directed pressure; and
    means for indicating the value of said inwardly-directed pressure, and thereby, a measure of the substance amount or density of the quantity of said fibers at the time said equilibrium is achieved.

2. An apparatus for determining the substance amount or density of quantities of fibers, comprising
    guide means including a duct for guiding said quantity of fibers through a space of predetermined cross section in said duct, said duct having an opening in the side thereof in communication with said space;
    a passive body disposed in said opening in said duct so as to partly extend into said duct and thereby be subjected to an outwardly-directed pressure from said fibers in the radial direction of said duct which is proportional to the elasticity of the fibers in said duct;
    means for subjecting said passive body to a variable inwardly-directed pressure in the radial direction of said duct to place said passive body in a state of equilibrium with respect to said outwardly-directed pressure; and
    means for indicating the value of said inwardly-directed pressure, and thereby, a measure of the substance amount or density of the quantity of said fibers at the time said equilibrium is achieved.
    wherein said passive body is a sphere.

3. An apparatus according to claim 2, wherein said opening in said duct comprises a conical bore.

4. An apparatus according to claim 3, wherein a groove is provided in the inner wall of said duct and extending from said opening in the direction of movement of said fibers.

5. An apparatus according to claim 4, wherein said groove is inclined to the axis of said duct so as to have maximum depth at the edge of said opening.

6. An apparatus for determining the substance amount or density of quantities of fibers, comprising
    guide means including a duct for guiding said quantity of fibers through a space of predetermined cross section, said duct having an opening in the side thereof;
    a passive body disposed in said opening in said duct so as to partly extend into said duct and thereby be subjected to an outwardly-directed pressure in the radial direction of said duct which is proportional to the elasticity of the fibers in said duct;
    means for subjecting said passive body to an inwardly-directed pressure in the radial direction of said duct to place said passive body in a state of equilibrium with respect to said outwardly-directed pressure including a nozzle through which compressed air is applied to said passive body; and
    means for indicating the value of said inwardly-directed pressure, and thereby, a measure of the substance amount or density of the quantity of said fibers.

7. An apparatus according to claim 6, wherein said indicating means comprises means for measuring the pressure of the compressed air applied to said passive body.

8. An apparatus for determining the substance amount or density of quantities of fibers, comprising
    guide means including a duct for guiding said quantity of fibers through a space of predetermined cross section, said duct having an opening in the side thereof;
    a passive body in the form of a sphere disposed in said opening in said duct so as to partly extend into said duct and thereby be subjected to an outwardly-directed pressure in the radial direction of said duct which is proportional to the elasticity of the fibers in said duct;
    means for subjecting said passive body to an inwardly-directed pressure to the radial direction of said duct to place said passive body in a state of equilibrium with respect to said outwardly-directed pressure, including a source of compressed air, a nozzle tube connected to receive compressed air from said source and having an end positioned in spaced relationship with said sphere to form a nozzle from which compressed air is directed at said sphere; and means for indicating the value of said inwardly-directed pressure, and thereby, a measure of the substance amount or density of the quantity of said fibers.

9. An apparatus according to claim 8, wherein said indicating means comprises means for measuring the pressure of said compressed air applied to said sphere.

10. An apparatus according to claim 9, further including a restrictor connected between said source of compressed air and said nozzle tube, said measuring means being connected downstream of said restrictor.

* * * * *